United States Patent [19]

Allen et al.

[11] 4,170,999
[45] Oct. 16, 1979

[54] DEMAND PACER HAVING REDUCED RECOVERY TIME

[75] Inventors: Kenneth R. Allen; Dennis Digby, both of Brooklyn Park; Alan Coombes, New Hope, all of Minn.

[73] Assignee: Biotronik Mess- und Therapiegeräte GmbH & Co., Berlin, Fed. Rep. of Germany

[21] Appl. No.: 917,131

[22] Filed: Jun. 19, 1978

[30] Foreign Application Priority Data

Aug. 19, 1977 [GB] United Kingdom ............... 34915/77

[51] Int. Cl.² ............................................. A61N 1/36
[52] U.S. Cl. ............................................. 128/419 PG
[58] Field of Search ................................. 128/419 PG

[56] References Cited

U.S. PATENT DOCUMENTS

| 3,557,796 | 1/1971 | Keller, Jr. et al. | 128/419 PG |
| 3,563,247 | 2/1971 | Bowers | 128/419 PG |
| 3,835,865 | 9/1974 | Bowers | 128/419 PG |
| 3,924,641 | 12/1975 | Weiss | 128/419 PG |

FOREIGN PATENT DOCUMENTS

| 2520729 | 11/1975 | Fed. Rep. of Germany | 128/419 PG |
| 2520730 | 11/1975 | Fed. Rep. of Germany | 128/419 PG |

*Primary Examiner*—William E. Kamm
*Attorney, Agent, or Firm*—Spencer & Kaye

[57] ABSTRACT

In a demand pacer, an input amplifier senses stimulating pulses and natural heart beat signals, and responsively thereto establishes control of a subsequent stimulating pulse. Charge accumulation on an output capacitor governs recovery time after each generated stimulating pulse. Respective first and second flip-flops, responsive to the input amplifier and the demand pacing logic, establishes a reduced recovery time, after each generated pulse, wherein charge accumulated on the output capacitor is dissipated.

4 Claims, 2 Drawing Figures

DEMAND PACER HAVING REDUCED RECOVERY TIME

TECHNICAL FIELD

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may or may not be implanted in the body, are well-known. Pacemakers can be classified into demand and non-demand types. A demand pacemaker only issues an artificial pulse if the heart does not produce its own satisfactory natural beat, whereas a non-demand pacemakers issues artificial stimulating pulses without regard to the presence or absence of a natural beat.

A demand pacemaker normally includes an input amplifier for receiving and amplifying electrical signals from the heart (which signals might result from either a natural beat or an artificial pulse which has just been generated by the pacemaker), a pacemaker control circuitry which receives the amplified signals and which causes a new artificial stimulating pulse to be generated (for transmission to the heart) only if the amplified signals, or lack thereof, show that an artificial stimulating pulse is required by the heart (i.e. on demand), and an output amplifier which receives and amplifies the artificial pulses generated by the control circuitry, for passage to the heart.

Many types of pacemaker control circuitry as described above are available. Some function on an analog basis to produce the accurately-timed artificial stimulating pulses, whereas several recent designs employ digital circuitry.

Of necessity, the input amplifier requires a high sensitivity and it has been found difficult to design an adequate amplifier that does not saturate for too long a period when an artificial pulse is transmitted to the heart by the output amplifier (this pulse being detected by the input amplifier). However, this need not be a problem provided the saturation period can be kept sufficiently short so that the input amplifier recovers in time to detect the presence or absence of the next expected natural beat.

The load which is driven by the output amplifier (the electrodes and the heart tissue itself) has capacitive properties and these, coupled with the capacitive components normally present in the output amplifier, can act to extend the length of any artificial pulse transmitted to the heart. Even if a sharp artificial pulse is generated by the pacemaker control circuitry, the capacitive effects at the output cause the trailing edge of the pulse to be extended so as to give a somewhat exponential decay back to zero. This extension of the output pulse is reflected at the input amplifier by increasing the length of time for which the latter remains saturated.

DISCLOSURE OF INVENTION

The present invention is concerned with alleviating this problem, so as to avoid these capacitive effects from increasing the saturation period of the input amplifier unnecessarily. This is accomplished, in this invention, by arranging for electrical energy to be fed into the pacemaker circuitry, at an appropriate moment after an artificial stimulating pulse is generated, in opposition to the energy stored by the capacitive components responsible for the extension of the artificial pulse. This has the effect of shorting these capacitive components, thus providing a much sharper falling edge for the output pulse and hence reducing the period of time spent for the input amplifier in saturation.

Preferably, the capacitive effects are cancelled by including an additional transistor in the output amplifier which is turned on at a predetermined time after an artificial stimulating pulse has been generated, which transistor then feeds current into the output circuit in opposition to the slowly decaying output pulse, thus returning the latter to zero at a faster rate.

Preferably, the pacemaker control circuitry includes a pulse generator for providing an artificial stimulating pulse, and means for resetting the pulse generator controlled either by an artificial pulse just generated or by a signal representative of a natural heart beat, so that the next artificial pulse is generated in timed relationship with the previous artificial pulse and only on demand. With such circuitry, the preferred additional transistor in the output amplifier can be arranged to be controlled by the reset provided to the pulse generator. In such a circumstance the reset determines the pulse width of the artificial pulse and by causing the additional transistor to compensate for the capacitive effects once the reset is applied, the sharp trailing edge of the artificial pulse is substantially maintained. A slow decay after the reset is applied is thus avoided, as therefore is an extension of the input amplifier saturation time.

BRIEF DESCRIPTION OF DRAWINGS

Preferred features of the invention will now be described with reference to the accompanying drawings in which.

BEST MODE OF CARRYING OUT THE INVENTION

Figure 1:
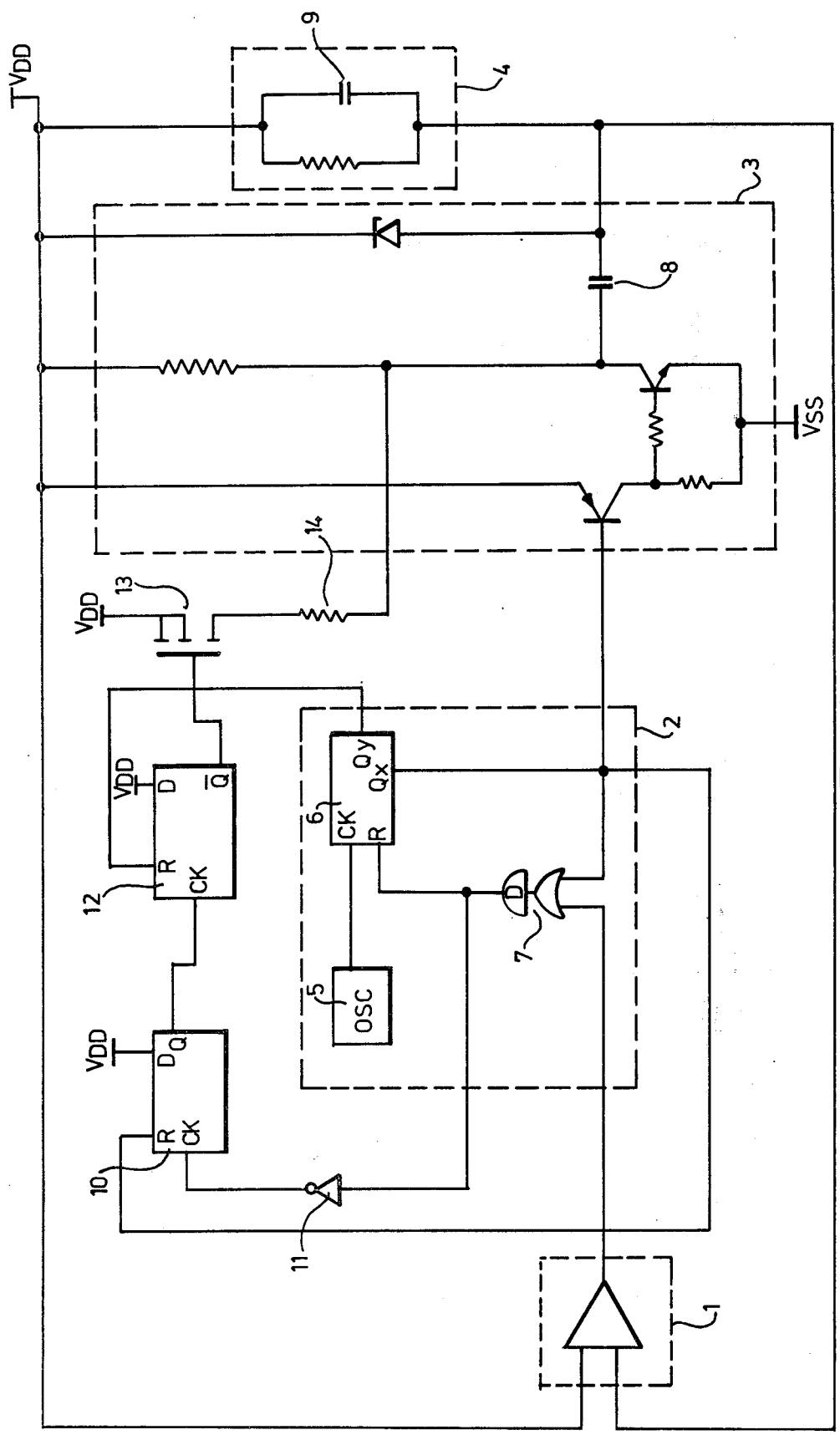
FIG. 1 illustrates schematically the electrical circuitry for a demand cardiac pacemaker.

Referring to the drawings, parts of the pacemaker are shown in three sections within separate dotted lines. The input amplifier is represented by section 1, the pacemaker control circuitry which generates artificial stimulating pulses on demand is represented by section 2, and the output amplifier is represented by section 3. The pacemaker load, i.e. the electrodes and the body tissue therebetween, is illustrated by a resistive/capacitive combination within a further section, section 4.

Many input amplifier, pacemaker control circuitry, and output amplifier combinations can be selected for use with the invention and therefore, to a large extent, many of the components of the illustrated pacemaker are shown functionally in block form. The particular selection of components for each block will be apparent to those skilled in the art.

Sections 1, 2, and 3 can be considered as representing a basic demand pacemaker. Oscillator 5 free runs and the particular artificial stimulating pulse rate appropriate to the patient is selected by counter 6 (the Qx output stage) for transmission to the output amplifier of section 3. If a natural heart beat is detected by the input amplifier of section 1, a reset circuit 7 for counter 6 (consisting of an OR gate followed by a delay D) is activated so that the artificial pulse count is not reached and no artificial pulse is generated. If no such natural beat is detected, the artificial pulse count is reached, and an artificial pulse is transmitted to the heart (section 4) by means of the output amplifier (section 3). In such a circumstance, the pulse width is determined by the delay D generated in the reset circuit 7—the counter 6 being reset at the termination of this delay.

Figure 2:
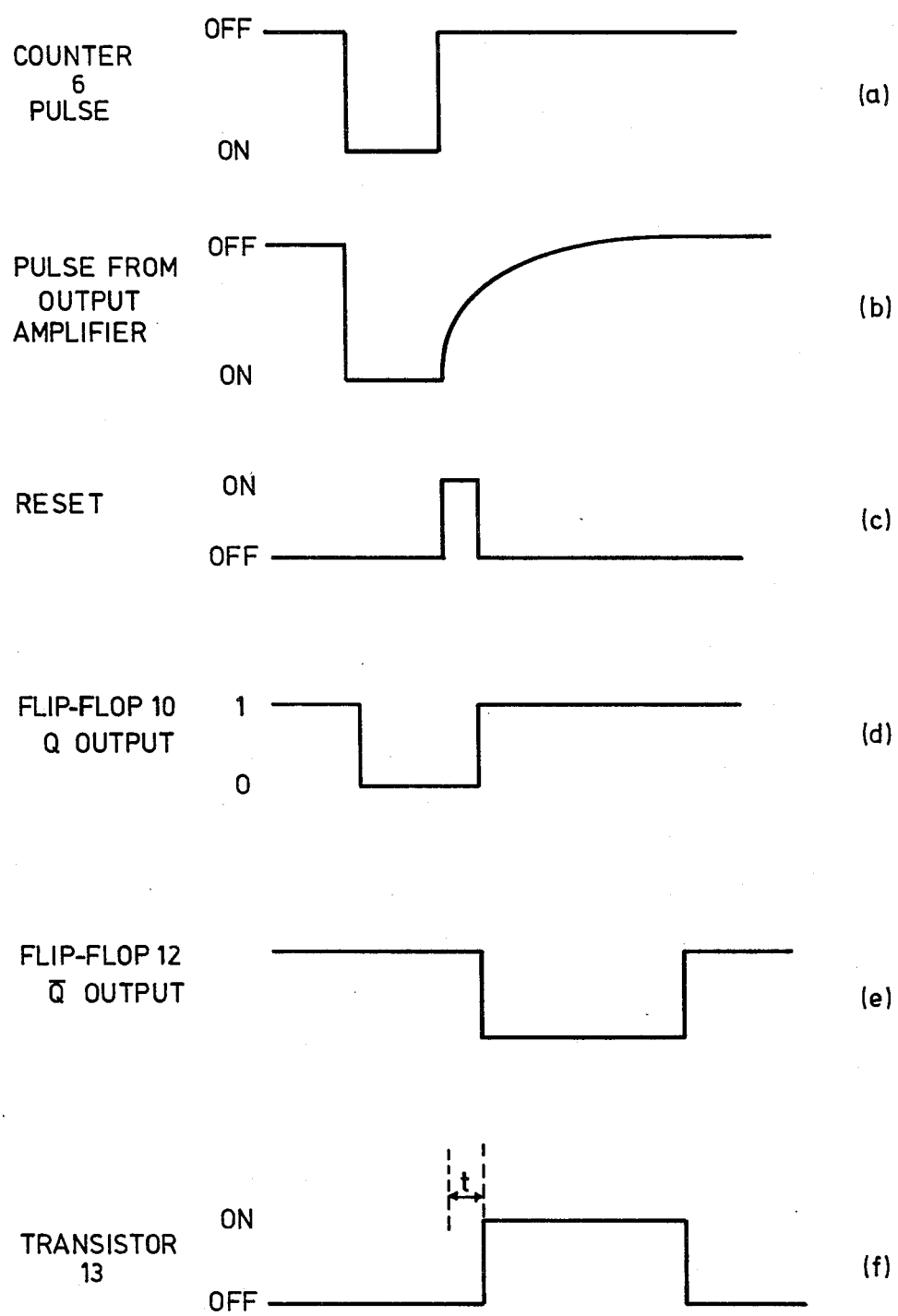
FIG. 2 represents a timing diagram for use with FIG. 1.

Although the output pulse generated by counter 6 has a fast rise and fall ((a) in FIG. 2), the capacitive effects in sections 3 and 4, particularly of capacitors 8 and 9, retard the fast fall of the artificial stimulating pulse at the heart ((b in FIG. 2) and this, as explained above, increases the time spent by the input amplifier in saturation.

To compensate for these capacitive effects, the pacemaker circuitry additionally includes a D flip-flop 10 which receives, at its clock input via an inverter 11, the reset pulse for counter 6. The reset input for flip-flop 10 is supplied by the counter 6 output, its D input is tied to the positive supply rail and its Q output clocks a second D flip-flop 12. Flip-flop 12 is reset by a system clock (derived from an appropriate stage Qy of counter 6) and has its D input tied to the positive supply rail. The $\bar{Q}$ output of flip-flop 12 controls the gate of a field effect transistor 13. The transistor 13 drain and source terminals are connected between the positive supply rail, via a resistor 14, to the output amplifier, adjacent output capacitor 8.

The operation of the input amplifier saturation-reducing circuit components will now be described.

When an artificial stimulating pulse is generated by counter 6 (see (a) in FIG. 2), this is not only transmitted to the output amplifier but it also resets flip-flop 10, whose Q output thus drops to low (see (d) in FIG. 2). After a delay generated by reset 7 which is appropriate to the artificial stimulating pulse width desired (see (c) in FIG. 2), counter 6 is reset and, at the termination of the reset pulse, flip-flop 10 is clocked via inverter 11. Clocking of flip-flop 10 causes its Q output to revert high and this clocks flip-flop 12. Clocking of flip-flop 12 causes its $\bar{Q}$ output to drop low (see (e) in FIG. 2) and this causes transistor 13 to conduct.

Current is then fed into the output amplifier by transistor 13 in a direction which increases the current flowing as a result of the slow decay of the capacitive components, and this acts to speed the decay, providing a faster return to the steady state condition, reducing the saturation time of the input amplifier.

Current continues to be fed by transistor 13 until flip-flop 12 is reset by an appropriately timed system clock pulse derived from counter 6. This reset causes the $\bar{Q}$ output of flip-flop 12 to revert high, thus switching transistor 13 off.

It will be observed from the above description that there is a delay between transistor 13 conducting and the end of the generated artificial pulse ("t" in (f), FIG. 2). This is to prevent a short circuit appearing across the voltage supply line at the output in the event of the counter 6 generating an output pulse simultaneously with transistor 13 conducting.

What is claimed is:

1. Demand-type cardiac stimulating apparatus comprising:
   (a) electrode means for coupling stimulating pulses to the heart;
   (b) an output amplifier stage for generating stimulating pulses for the heart, said output stage having an output capacitor connected to said electrode means, said output stage having an output impedance recovery interval established, after each stimulating pulse generation, in substantial part by the accumulation and subsequent dissipation of charge on said output capacitor;
   (c) input amplifier means, responsive to signals from said output stage and to naturally occurring heart beat signals, for producing a control signal relative to the generation of a next subsequent stimulating pulse;
   (d) logic means, responsive to said control signal, for selectively energizing said output amplifier to generate a stimulating pulse based on predetermined demand pacing criteria;
   (e) and the improvement comprising means for shortening said recovery interval including
      (i) first bistable means, conditioned to a first enabling output state by said logic means at a predetermined time after each said selective energizing;
      (ii) second bistable means, clocked to an enabling output state by said enabling state of said first bistable means, said enabling output state of said second bistable means being terminated by said logic means after a second predetermined duration, said second duration defining a reduced recovery interval of said output stage, and
      (iii) transistor means, responsive to said second bistable means and energized during said second duration, for dissipating charge on said output capacitor, and thereby establishing a shortened recovery interval for said output stage.

2. Apparatus as described in claim 1 wherein said logic means comprises an oscillator, counter means for counting pulses from said oscillator, and delay means, energized by said control signal or by a first predetermined count at said counter, for producing an output pulse a predetermined delay time after being energized, wherein said first bistable means is reset by said first predetermined count of said counter, and is clocked to its said first enabling output state by said output pulse from said delay means, and wherein said second bistable means is reset by a second predetermined count, later than said first count, at said counter means.

3. Apparatus as described in claim 1 wherein said counter means is reset by each output pulse from said delay means.

4. Apparatus as described in claim 3 wherein said bistable means are D-type flip-flops, having their respective D-inputs connected to a positive voltage supply, said output of said first flip-flop being its Q output, and said output of said second flip-flop being its Q output.

* * * * *